(12) United States Patent
Ross

(10) Patent No.: US 6,652,444 B1
(45) Date of Patent: Nov. 25, 2003

(54) SUPPLEMENTAL DIABETIC TREATMENT METHOD

(76) Inventor: Jesse Ross, 321 E. Shore Rd., Great Neck, NY (US) 11023

(*) Notice: Subject to any disclaimer, the term of this patent is extended or adjusted under 35 U.S.C. 154(b) by 0 days.

(21) Appl. No.: 10/217,585

(22) Filed: Aug. 13, 2002

(51) Int. Cl.⁷ .................................................. A61N 1/00

(52) U.S. Cl. ............................................. 600/9; 600/15
(58) Field of Search ................ 600/9–15; 128/897–98; 607/100, 106

(56) References Cited

U.S. PATENT DOCUMENTS 6,589,159 B2 * 7/2003 Paturu ........................ 600/15

* cited by examiner

Primary Examiner—John P. Lacyk
(74) Attorney, Agent, or Firm—Myron Amer PC

(57) ABSTRACT

An electromagnetic treatment available to diabetics to supplement current treatment of diet, medication and exercise now made cognitive to be availed of from the common practice of monitoring of glucose blood content and observing a reading in excess of 200, thus using to further advantage the knowledge learned by monitoring glucose blood content.

1 Claim, 2 Drawing Sheets

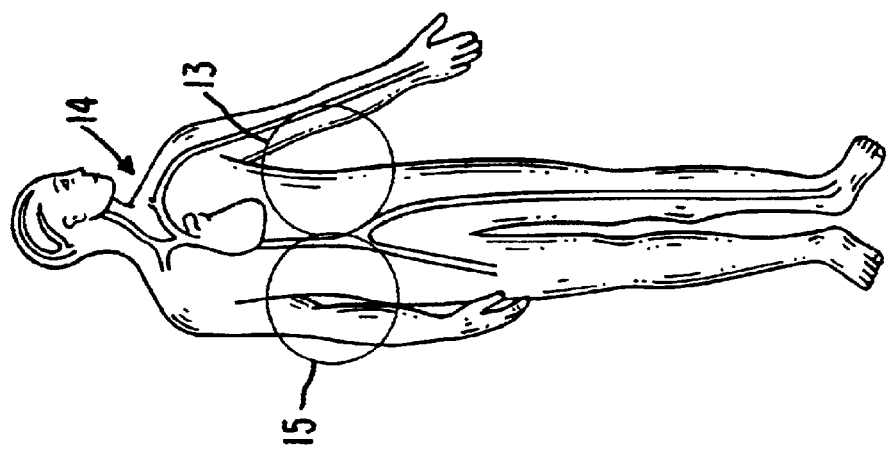
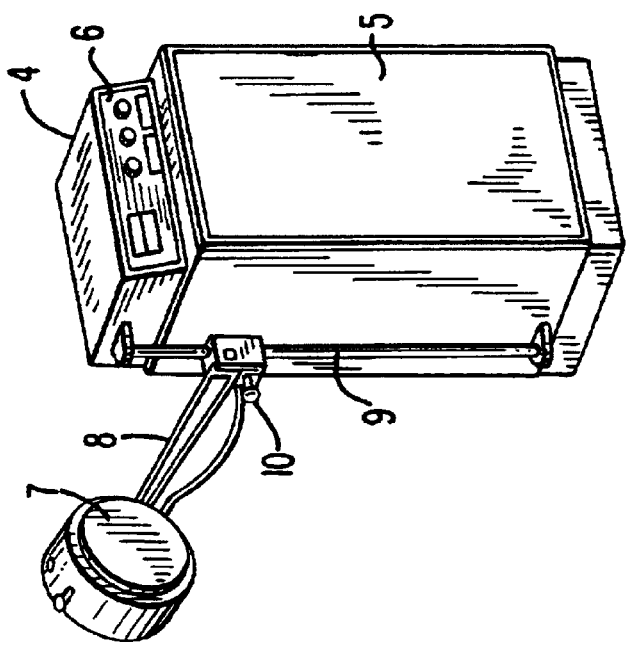
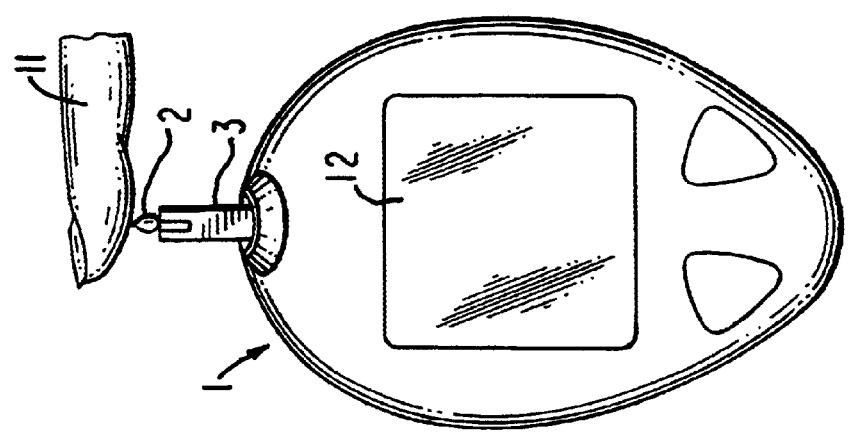

SUPPLEMENTAL DIABETIC TREATMENT METHOD

The present invention relates generally to improvements for treating Diabetes Mellitus, the improvements, more particularly, supplementing the current treatment requiring patient participation with electromagnetic field treatment, both correlated to monitoring of glucose blood content.

BACKGROUND OF THE INVENTION

Field of the Invention

Proposed is an improved diabetic treatment method supplemental to a known treatment method using patient diet, medicine intake and exercise, wherein that being used in the known treatment method aptly constitute liver and pancreas-affecting conditions, and according to current practice are conditions monitored by glucose blood content readings.

Diabetes Mellitus is a worldwide chronic disorder of glucose hemostasis which afflicts six percent of the general population and is the eighth leading cause of death in the United States being a disease that affects the way the body uses food. It causes sugar levels in the blood to be too high.

Normally, during digestion, the body changes sugars, starches, and other foods into a form of sugar called glucose. Then the blood carries this glucose to cells throughout the body. There, with the help of insulin (a hormone), glucose is changed into quick energy for immediate use by the cells or is stored for future needs. This process of turning food into energy is crucial, because the body depends on food for every action, from pumping blood and thinking to running and jumping.

In diabetes, something goes wrong with the normal process of turning food into energy. Food is changed into glucose readily enough, but there is a problem with insulin. In one type of diabetes, the pancreas cannot make insulin. In another type the body makes some insulin but either makes too little or has trouble using the insulin (or both). When insulin is absent or ineffective, the glucose in the bloodstream cannot be used by the cells to make energy. Instead, glucose collects in the blood, eventually leading to the high sugar levels that are the hallmark of untreated diabetes.

It is thus the current practice for a diabetic to use a finger prick to produce a droplet of blood that is absorbed in a test strip of a monitor of known construction and of an operating mode effective to display a numeric reading of the diabetic's glucose blood content which at 90–130 in the morning and 150–160 two hours before or after an evening meal are considered acceptable, and if in excess of an acceptable reading dictates the diabetic participating in a known treatment of reducing liver and pancreas-affecting conditions by proper diet, such as eating sugar-free or low sugar content foods, medicine input, such as Metformin HCL in pill or capsule form in prescribed doses and intervals, and partaking of exercise, such as jogging and walking.

SUMMARY OF THE INVENTION

The basic functions of the liver as are known can be divided into (1) its vascular functions for storage and filtration of blood, (2) its metabolic functions concerned with the majority of the metabolic systems of the body, and (3) its secretory and excretory functions that are responsible for forming the bile that flows through the bile ducts into the gastrointestinal tract. Underlying the present invention is the recognition that a breakdown of the liver function of "filtration of blood" is also dictated by an excessive monitored glucose blood content reading, in this case an exemplary reading of 200 or higher, such as 220–300, and thus the monitoring which occurs preparatory to implementation of the known treatment previously noted is also used to advantage to implement a supplemental treatment method, whereas heretofore a diabetic treatment had primarily only one focus.

Broadly, it is an object of the presort invention to overcome the foregoing and other shortcomings of the prior art.

More particularly, it is an object of the present invention to supplement the reduction of liver and pancreas-affecting conditions with a treatment affecting an increase or enhancement of the blood filtering function thereof by electromagnetic field impingement on these organs, all as will be better understood as the description proceeds.

BRIEF DESCRIPTION OF THE DRAWINGS

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective view of a glucose blood content monitor used in the practice of the method of the present invention;

FIG. 2 is a perspective view of an apparatus for generating an electromagnetic field also used for practicing the method of the present invention;

FIG. 5 is a graphic of blood circulation.

DESCRIPTION OF THE PREFERRED EMBODIMENT

Figure 4:
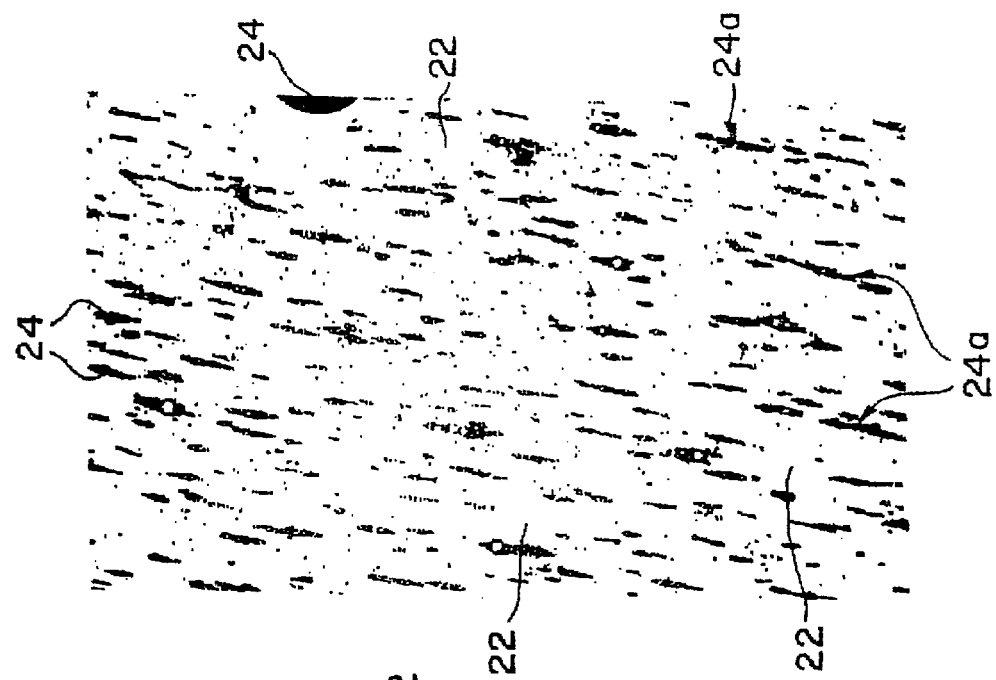
FIG. 4 is another microphotograph illustration of the blood of FIG. 3, but after subjection to the high frequency oscillation and showing a pearl chain formation of the nutritive blood elements.

Illustrated in FIG. 1 is a monitor, generally designated 1, currently in popular use, of known construction and operating mode effective to absorb a droplet of blood 2 in an end of a test strip 3 extending from the monitor and analyze the blood, presumably from a diabetic 11, and display a number (not shown) at site 12 which indicates the glucose blood content of the provider 11. A monitor suitable for use as described is commercially available from Life Scan, Inc. of Milpitas, Calif. 95035.

If the displayed number at 12 is slightly in excess of what is deemed acceptable, it will be understood that it will implement a known diabetic treatment of patient participation in diet management, medication input and moderate exercise.

If the displayed number is 200 plus, it will be understood that it dictates a diabetic treatment addressing liver and pancreas blood-filtering functioning as a supplement to the known diet, medication and exercise treatment. To this end, and as shown in FIG. 2, is an athermapeutic apparatus for the generation of pulsed high frequency oscillations to which a diabetic patient is subjected of a type which is now well known to the art wherein the pulse frequency and duration is of such nature that the total time period during which electrical energy is actually induced into the body of a patient is so short that despite the comparatively high instantaneous energy level of the pulsed power it is unaccompanied by heat generation because the time for heat dissipation is many times longer than the heat accumulation. The athermapeutic apparatus 4 as therein shown comprises a cabinet 5 provided with a control panel 6, for regulating the pulse repetition rate and pulse duration, timer setting, etc., and having a treatment head 7. Such treatment head is carried by an arm 8 to which it is pivotally connected, and with the arm in turn being reciprocally and axially movable on a tubular support 9 and secured in any desired adjusted position relative to the support 9 by a locking screw 10.

Apparatus 4 will be understood to generate an electromagnetic field having a pulse duration and frequency which is fixed at sixty-five microseconds and for pulse frequencies of from eighty to six hundred pulses per second, so that even at its maximum setting the total peak energy of nine hundred seventy-five watts maximum is of such short duration that the average power is only twenty-five to forty watts. Accordingly, at the maximum pulse rate of six hundred pulses per second the rest period between the pulses is approximately twenty-four times as great as the duration of each pulse, so that any heat that might be accumulated in the patient during the occurrence of the pulse has many times longer for its dissipation, thereby providing a treatment which is not harmful to the patient.

In the treatment use of the apparatus 4, the electromagnetic filed utilized might typically have the following specific parameters:

1. A frequency of 27.12 megahertz (11 meter band);
2. A pulse repetition rate of 80 to 600 pulses per second;
3. A pulse width of 65 microseconds;
4. A power range per pulse, of between 293 and 975 watts;
5. A duty cycle between ½ of 1% to 3.9%; and
6. A square pulse, with a rise and fall time less than 1%.

Underlying the present invention is the recognition that the generated electromagnetic field of apparatus 4 can be used to advantage to increase blood flow or circulation without any increase in the patient's heartbeat or any dilution of the patient's blood as might adversely impact on the health of the patient.

To the above end, to a patient 14 the head 7 of apparatus 4 is positioned in electromagnetic field penetrating relation to a selected body location of the patient. The basis of selection of the body location is to make accessible to the generated magnetic field, in this case initially, the liver and the left pancreas lobe at location 13, and subsequently, the right pancreas lobe at location 15 and at each location a time interval of electromagnetic field penetration of between 15 to 20 minutes in the judgment of the operator of the apparatus 4.

Figure 3:
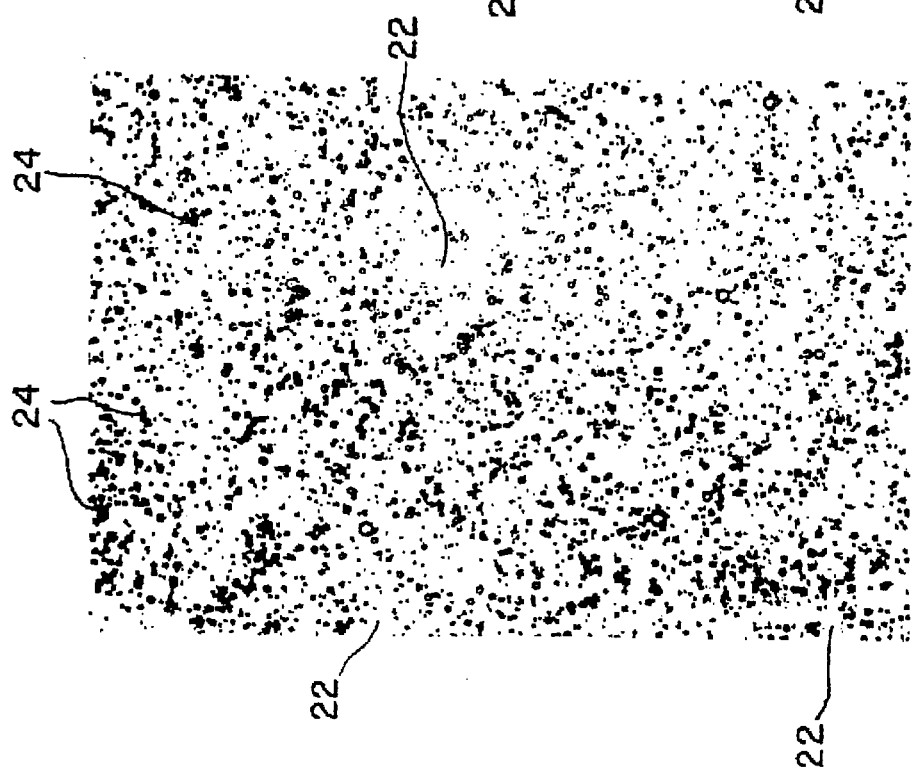
FIG. 3 is an illustration of a microphotograph of blood prior to the subjection to high frequency oscillation.

The result of the impingement of the electromagnetic field on the blood is best understood from FIGS. 3 and 4, to which reference should now be made. Blank or unoccupied areas, individually and collectively designated 22, will be understood to be the fluid content of the blood, and the occupied areas, also individually and collectively designated 24, will be understood to be the nutritive elements of which the blood is composed, such as lymph, chyle, plasma, etc.

By comparison of FIG. 3 before subjection to the electromagnetic field, to FIG. 4, after subjection, it should be readily observable that the pattern of FIG. 3 is a random dispersion of the blood fluid and nutritive elements contents 22, 24, and that in FIG. 4 the nutritive elements 24 have assumed a chain-like formation, more particularly designated 24A, which formulation is known in the parlance of the art as a "pearl chain" formation.

A physical noteworthy attribute provided by the pearl chain formulation 24A is its longitudinal orientation which, during blood flow in the longitudinal direction is flow with minimum resistance, which is manifested as an increase in blood flow or velocity.

More particularly, at rest the velocity, designated 30, is 5,000 ml per minute, and when in a testing run the rate of blood velocity was measured to increase 1.75 times the testing pulse, which increased from the base rate of 100. It was noted that the increase occurs during treatment and is maintained 1 to 8 hours.

In practice, it has been found that the supplemental treatment of electromagnetic field impingement of the liver and pancreas lobes significantly reduces the monitored glucose blood content reading from 200 to an acceptable level and is believed to be attributable to enhanced liver and pancreas filtering and distribution of glucose by these organs, and without which enhancement the patient participation treatment which would require a longer duration of unacceptable glucose content would put the patient at risk of deleterious metabolic derangement such as end-organ damage or the like.

An athermapeutic apparatus 4 suitable for use as described is commercially available from Diapulse Corp. of America located at Great Neck N.Y.

While the apparatus for practicing the within inventive method, as well as the method herein shown and disclosed in detail, is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. An improved diabetic treatment method supplemental to a known treatment method using patient diet, medicine intake and exercise and monitored glucose blood content readings, said improvement comprising the steps of monitoring in selected continuous relation glucose blood content, participating by patients below a monitored reading of 200 in said diet, medicine and exercise treatment to contribute to producing liver and pancreas-affecting conditions responding to said diet, medicine and exercise, and supplementing diabetic treatment at a monitored reading in excess of 200 addressing liver and pancreas blood-filtering functioning by generating an electromagnetic field onto a first selected site for treatment for a first selected time duration with operating parameters of a frequency of 27.12 megahertz, a pulse repetition rate of 80 to 600 pulses per second, a pulse width of 65 microseconds, a power range per pulse of between 293 and 975 watts, a duty cycle between ½ of 1% to 3.9%, and a square pulse, with a rise and fall time less than 1%, impinging blood in said first selected site for treatment with said generated electromagnetic field, aligning blood components including lymph, chyle and plasma contents thereof in longitudinal relation to each other with said generated electromagnetic field, and flowing in a longitudinal direction said blood with said aligned contents thereof through said treatment site, such that blood flow at said first treatment site is increased to flow rate enhancing blood-filtering function, said first selected site being externally adjacent the liver and right lobe of the pancreas and said first selected time duration is 15 to 20 minutes, and repeating said generating an electromagnetic field onto a second selected site for treatment for a second selected time duration such that there is additional enhancing of blood-filtering function, said second selected site being externally adjacent the left lobe of the pancreas and said second selected time duration is 15 to 20 minutes, whereby there is diabetic treatment of reduction of conditions requiring a liver and pancreas filter function and of enhancing condition of said filter function, both correlated to monitoring of glucose blood content.

\* \* \* \* \*